(12) United States Patent
McGhin et al.

(10) Patent No.: US 8,063,343 B2
(45) Date of Patent: Nov. 22, 2011

(54) HEATED BREATHING CIRCUIT DETECTION (75) Inventors: Cary E. McGhin, Sugar Hill, GA (US); Ashok Mahadevan, Alpharetta, GA (US); Robert L. Snyder, Suwanee, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1058 days.

(21) Appl. No.: 11/927,004

(22) Filed: Oct. 29, 2007

(65) Prior Publication Data
US 2009/0107982 A1 Apr. 30, 2009

(51) Int. Cl.
*H05B 1/02* (2006.01)
(52) U.S. Cl. .... 219/497; 219/505; 219/481; 128/203.17
(58) Field of Classification Search .................. 219/494, 219/497, 496, 505, 501, 481; 128/203.17, 128/204.17, 203.26, 201.13
See application file for complete search history.

(56) References Cited

U.S. PATENT DOCUMENTS

| | | | |
|---|---|---|---|
| 4,277,671 A | 7/1981 | Mori et al. | |
| 4,598,195 A * | 7/1986 | Matsuo | 219/497 |
| 4,978,837 A * | 12/1990 | Eggleston | 219/497 |
| 5,367,146 A * | 11/1994 | Grunig | 219/497 |
| 5,452,725 A | 9/1995 | Martenson | |
| 5,537,996 A | 7/1996 | McPhee | |
| 5,811,765 A * | 9/1998 | Nakagawa et al. | 219/497 |
| 5,943,473 A | 8/1999 | Levine | |
| 6,078,730 A | 6/2000 | Huddart et al. | |
| 6,455,820 B2 | 9/2002 | Bradenbaugh | |
| 6,598,604 B1 * | 7/2003 | Seakins | 128/203.17 |
| 6,988,497 B2 | 1/2006 | Levine | |
| 7,106,955 B2 | 9/2006 | Thudor et al. | |
| 7,140,367 B2 * | 11/2006 | White et al. | 128/204.17 |
| 2002/0083947 A1 | 7/2002 | Seakins | |
| 2002/0112725 A1 | 8/2002 | Thudor et al. | |
| 2003/0079748 A1 | 5/2003 | Seakins | |
| 2003/0154977 A1 | 8/2003 | White et al. | |
| 2004/0221844 A1 | 11/2004 | Hunt et al. | |
| 2008/0054497 A1 | 3/2008 | Bradley et al. | |
| 2008/0054500 A1 | 3/2008 | Bradley et al. | |
| 2009/0065002 A1 | 3/2009 | Hunt | |

FOREIGN PATENT DOCUMENTS

EP 1127583 A2 12/2000
(Continued)

OTHER PUBLICATIONS

Partial European Search Report for counterpart European Application No. 08167299.0-2320 (4 pages).

(Continued)

*Primary Examiner* — Mark Paschall
(74) *Attorney, Agent, or Firm* — Wood, Herron & Evans, LLP (57) ABSTRACT A heated breathing circuit detection system verifies the proper set up and connection of a breathing circuit to a heater unit of a humidification system. The detection system automatically detects that the breathing circuit is connected to the heater unit, and the nature of the heating circuit(s) thereof. In one embodiment, the resistance of the heating circuit(s) is determined and compared to an expected resistance or range of acceptable resistances to determine if the heater circuit(s) is properly or actually attached and properly operating. The humidification system also has the ability to determine the delivery mode of the breathing circuit, i.e., whether a single inspiratory limb, or both inspiratory and expiratory limbs, is connected to the heater unit.

30 Claims, 7 Drawing Sheets

FOREIGN PATENT DOCUMENTS

| | | |
|---|---|---|
| EP | 1731188 A2 | 6/2006 |
| WO | WO2006019323 A1 | 2/2006 |
| WO | 2006092001 A1 | 9/2006 |
| WO | 2008055308 A1 | 5/2008 |

OTHER PUBLICATIONS

Extended European Search Report in counterpart European Application No. 08167299 (10 pages).

Manual for Fisher & Paykel Model Nos. MR700, MR720, MR730 Respiratory Humidifiers (Mar. 1998) (48 pages).

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Brochure for Hudson RCI Humid-Heat® (6 pages).

Operating Manual for Fisher & Paykel Model Nos. MR700, MR720, MR730 Respiratory Humidifiers (Mar. 1994) (46 pages).

Instruction Sheet for Airlife® Single Heated Adult Respiratory Circuit (2 pages) (date uncertain).

Cardinal Health RT110 Data for Circuits, reprinted from the internet Jun. 3, 2006 (2 pages).

Fisher & Paykel 900MR561 Temperature Probe Label (one page) (date uncertain).

Fisher & Paykel Airway Temperature Probes Instructions for Use (3 pages) (2003).

Cat. RT110 Insert for Airlife™ Adult Respiratory Circuit—Heated (one page) (undated).

\* cited by examiner

FIG. 4

HEATED BREATHING CIRCUIT DETECTION

FIELD OF THE INVENTION

The present invention relates to heated breathing circuits in a respiratory system, and more particularly, to detection of the heated breathing circuit.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. The breathing circuit may also include an expiratory limb hose or conduit to carry expelled air and other gas(es) from the patient back to the ventilator.

It is typically desired to warm and impart humidity to the breathable gas before it is provided to the patient. For that purpose, many respiratory systems include a humidification system including a heater unit and a disposable water chamber adapted to be heated by the heater unit. The heater unit supports a hot plate heater, which may be comprised of one or more heating elements and a metal plate defining a hot plate. A wall of the chamber, such as the bottom surface of the chamber, is thermally conductive. The chamber is removably supported on the heater unit with the thermally conductive surface in thermal contact with the hot plate of the heater unit to thus heat the water in the chamber. The chamber may be manually refillable, or there may be a water source to selectively fill the chamber as it empties. The breathable gas is coupled to the chamber and is passed through the chamber to be heated and humidified. Examples of heater units, chambers and vented water supplies are shown in U.S. Pat. Nos. 6,988,497 and 5,943,473; and co-pending U.S. patent application Ser. Nos. 11/469,086 and 11/469,113, both filed Aug. 31, 2006.

The inspiratory limb carries the heated and humidified gas to the patient and the expiratory limb, if present, carries exhaled air and possibly other gases from the patient. The inspiratory limb and the expiratory limb may each be provided with a heater circuit to add heat to the gas passing through the limb. The heater circuit may be in the form of one or more elongated, and possibly coiled, heater wires running along the limb, such as through the interior of the limb. An example of a breathing circuit with heated limbs is shown in U.S. Pat. No. 6,078,770. The heater unit typically houses the necessary electrical and electronic components to regulate the temperature of the hot plate, as well as the heater circuit(s) of the inspiratory and/or expiratory limbs of the breathing circuit. To that end, the temperature of the gas passing through the breathing circuit may be monitored at various locations, two examples of which are at the outlet of the chamber (i.e., the inlet to the inspiratory limb) and/or at the outlet of the inspiratory limb (i.e., at the patient). The temperature of the hot plate may also be monitored. The temperature readings obtained are utilized by the heater unit for purposes of regulating the various heating components.

With respect to the heating circuits, the heater unit regulates the power thereto in relation to the resistance of the heating circuit based on the watt density and length of the wires employed in the heating circuit, for example. There are many types of breathing circuits that might be employed, depending on the nature of the respiratory system and its application. By way of example, some breathing circuits have only an inspiratory limb; some have both inspiratory and expiratory limbs. In some situations, one or both of the limbs has a heater circuit. Moreover, the nature of the heating circuit and the limbs may differ depending upon whether the breathing circuit is for adult, pediatric or neonatal application. In each situation, the heater unit and breathing circuit have to properly matched, so that the heater unit is set up appropriately depending upon whether or not a respective heater circuit is present or to be used, and if so, for the specifics of that heater circuit, such as the resistance thereof. The user or operator of the heater unit must thus take care to select a proper breathing circuit, to properly connect the heater circuit(s) to the heater unit, and to properly set up the heater unit for that breathing circuit. Failure to properly set up or connect to the heater circuit, or using an incorrectly matched breathing circuit, can lead to serious adverse consequences. Accordingly, additional levels of protection are desirable to ensure proper selection, connection and set up of breathing circuits to heater units to avoid the adverse consequences of an incorrectly matched or connected breathing circuit.

SUMMARY OF THE INVENTION

The present invention provides a heater unit adapted to avoid the adverse consequences of an incorrectly matched or coupled breathing circuit. To that end, and in accordance with the principles of the present invention, the heater unit is adapted to automatically detect that a heated breathing circuit is coupled thereto, and the nature of the heating circuit(s) thereof. In one embodiment, the heater unit is adapted to selectively attempt to power the heater circuit in the inspiratory limb in order detect the current flowing therethrough and from which the resistance of the heater circuit may then be determined. The resistance is then compared to an expected resistance or range of acceptable resistances to determine if the heater circuit is properly or actually attached and properly operating, as well as to determine if it is the correct one for the particular set-up of the heater unit. If the correct heater circuit is properly attached, the determined resistance will match to an expected resistance or be within a range of acceptable resistances such that the heater unit is determined to be properly set up for operation and heating can commence as desired. If, however, an incorrect resistance is determined, a failure is detected and an alarm may be given and the heater unit will not proceed with heating. In that regard, the resistance could be in error if the wrong limb is used such that the heater circuit attached to the heater unit is incorrect, or if the heater circuit has an open or short in it, or if coupling of the heater circuit to the heater unit is not properly established. As a result, the heater unit is adapted to detect proper attachment of a proper heating circuit in relation to the heater unit set-up thus reducing the risk of operator error. Further, error is reduced because the heater unit may detect defects or breaks in the heater circuit.

The heater unit may be further adapted to selectively attempt to power the heater circuit in the expiratory limb in order detect the current flowing therethrough and from which the resistance of the heater circuit may then be determined. The resistance is then compared to an expected resistance or range of acceptable resistances to determine if the heater circuit is properly or actually attached and properly operating, as well as to determine if it is the correct one for the particular set-up of the heater unit. As with the inspiratory limb, if the correct heater circuit is properly attached, the determined resistance will match to an expected resistance or be within a range of acceptable resistances such that the heater unit is determined to be properly set up for operation and heating can commence as desired. If, however, an incorrect resistance is determined, for any of the same reasons given above in relation to the inspiratory limb, a failure is detected and an alarm may be given and the heater unit will not proceed with heating.

Advantageously, the detection of the heated breathing circuit limb(s) is undertaken during a power-up sequence of the heater unit, so that errors can be detected and alarms given while the user is likely at the heater unit and before normal heating is expected to be undertaken. Indeed, the detection can be undertaken before the heater circuit(s) are energized to a level required for heating of gas passing therethrough.

A zero crossing detector can be used to determine if there is a presence of inspiratory and expiratory limbs. A zero crossing voltage divider method is used to generally detect the presence of both inspiratory and expiratory limbs while the unit is operating, i.e. delivering power to the limbs to detect failure or removal of the limbs. When there is no drive voltage, zero crossings will be detected if the impedance of the limbs is not present. Zero crossings will not occur if the limbs are attached. When there is a drive voltage zero crossings will always occur. This configuration provides the capability to detect an open limb heater circuit due to failure or removal of the limb from heater unit. Limb presence can be detected without having to energize the limb heater circuit.

A Hall Effect sensor can be used to isolate the AC waveform applied to the heater elements from the transformer or power supply for determination of the resistance of the limb. The present invention provides the ability to determine wire resistance over a small number of AC cycles using actual current path current measurement. The fast capability of this approach allows the wire impedance to be determined in standby mode prior to operating without appreciably heating the air path. Zero crossing detectors detect both when the waveform has crossed from a negative to a positive voltage and the period length of a cycle. Samples are taken to measure the Hall Effect sensor output voltage, which is directly proportional to the magnitude of the current flowing through the limb. More samples measure the DC power supply voltage, which is directly proportional to the magnitude of the voltage applied to the limb heater circuit. The samples are averaged to obtain the peak limb heater circuit current and the peak limb heater circuit voltage. By turning on only one limb (expiratory or inspiratory) at a time, the resistance of each limb heater element can be determined in an individual manner. This instantaneous limb heater circuit resistance value is used to determine the nature of the limb attached.

To distinguish if the heater unit should be operating in single limb mode, where only the inspiratory limb heater circuit is required, or dual limb mode, where both the inspiratory and the expiratory heater circuits are required, in accordance with another aspect of the present invention a coupler is used. The coupler, for inspiratory limb heater circuit operation only, contains different limb heater circuit detection identification bits, than the limb heater circuit coupler for inspiratory and expiratory heater circuit operation. In other words, the limb heater circuit detection identification bits are provided in limb heater circuit coupler to determine delivery mode, i.e. non-heated wire, single limb or dual limb.

Advantageously, the breathing circuit includes a first electrical connector adapted with internal jumpers and interconnections to correspond to the type of breathing circuit, i.e., whether it has only a heated inspiratory limb or has heated inspiratory and expiratory limbs, along with appropriate interconnections to couple the heater circuit of the heated limb(s) to the heater unit when the electrical connector is plugged into a second electrical connector of the heater unit adapted to mate with the breathing circuit first electrical connector. To that end, in one embodiment, two of the contacts of the second electrical connector may be coupled, such as via respective resistors, to a first power supply rail to cause those contacts to normally present a digital a logical value normally interpreted by the processor as indicating that no heater circuit is attached. If the inspiratory limb includes a heater circuit, a jumper in the first electrical connector, when attached to the second electrical connector, will connect the appropriate contact to the other power supply rail to pull the contact to the opposite digital logical value which the processor will interpret as indicating that an inspiratory limb heating circuit is attached. If a heated expiratory limb is also present, a further jumper in the first electrical connector will, when attached to the second electrical connector, also pull the other contact to the other power supply rail so as to also present thereat the opposite digital logic value which the processor will interpret as indicating that an expiratory limb heated circuit is attached.

In those situations where the heater unit is set up for a breathing circuit having at least a heated inspiratory limb, if the first and second electrical connectors being coupled does not result in the appropriate contacts being pulled to the correct logical value, an alarm may be given and the heater unit will not run to provide normal heating. Similarly, if the heater unit is set up for a breathing circuit having both a heated inspiratory limb and a heated expiratory limb, both contacts should be pulled to proper digital logic value, if not an alarm may be given and the heater unit will not run to provide normal heating.

By virtue of the foregoing, there is thus provided a heater unit adapted to avoid the adverse consequences of an incorrectly matched or coupled breathing circuit. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
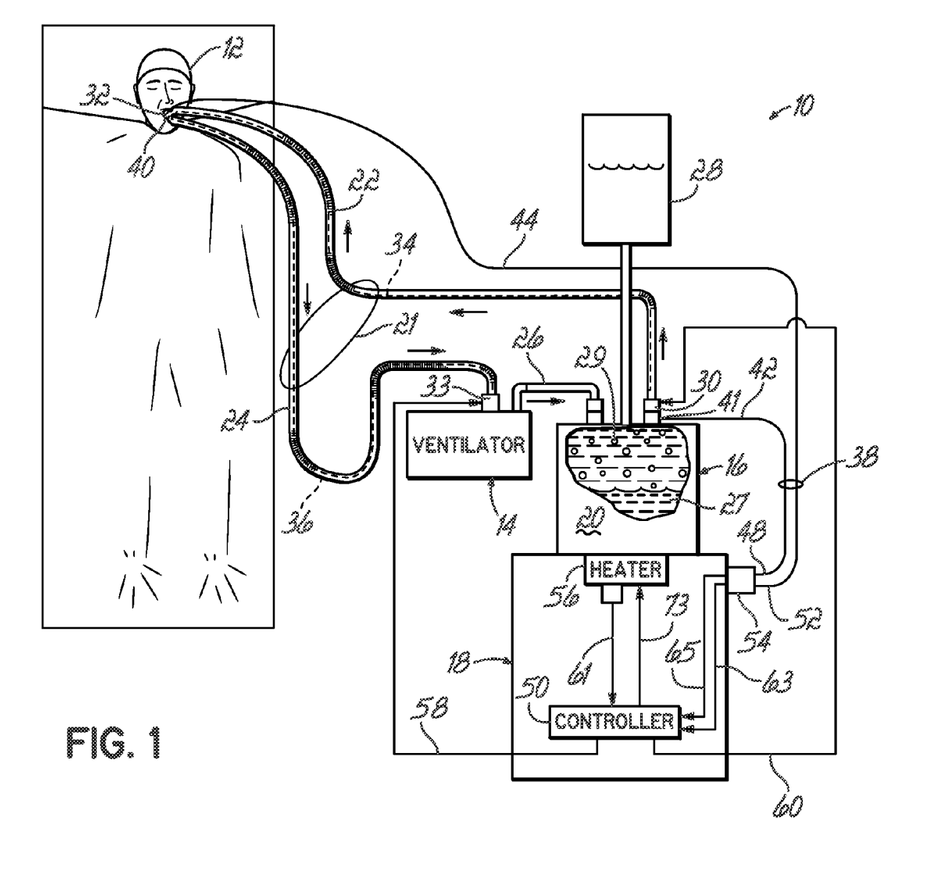
FIG. 1 is a schematic diagram of a respiratory system having a heater unit incorporating a heated breathing circuit detection feature in accordance with the principles of the present invention.

FIG. 1 is an exemplary respiratory system 10 for supplying breathable gases to patient 12. In the illustrated embodiment, respiratory system 10 includes ventilator 14, humidification system 16 operatively associated to heater unit 18, a container within humidification system 16 capable of being heated for water such as a removable chamber 20, and a breathing hose or conduit system 21 having a first elongated hose or conduit comprising the inspiratory limb 22 and a second elongated hose or conduit comprising the expiratory limb 24. Ventilator 14 drives breathable gas, such as oxygen, anesthetic gas and/or air, through gas conduit 26 and into an air inlet of chamber 20. Water 27, or any other such liquid used for the purpose of humidification, is received in chamber 20, either by being poured in manually or automatically from a water supply 28 such as a bag or bottle, and which may be vented. Chamber 20 is heated by heater unit 18 and thus heating water 27 therein. Heated water vapor 29 may also be produced within chamber 20 above the level of water 27 therein. The gas from conduit 26 passes over or through the heated water 27 and/or through heated water vapor 29 to become heated and humidified before exiting the chamber 20 as heated and humidified gases. Examples of humidification systems are shown in aforementioned U.S. Pat. No. 6,988,497 and co-pending U.S. patent application Ser. No. 11/469,086 filed Aug. 31, 2006 and Ser. No. 11/469,113 filed Aug. 31, 2006, the disclosures of all three of which are incorporated herein by reference in their entireties.

The heated and humidified gas flows from chamber 20 to patient 12 by passing through inspiratory limb 22. A connecting member or joint 30 couples a first end of inspiratory limb 22 to chamber 20, and a second end of inspiratory limb 22 is coupled to breathing attachment 32 that facilitates delivery of the gas passed there through to patient 12. Breathing attachment 32 may couple to an invasive apparatus such as an endotracheal tube, or a non-invasive apparatus such as a mask (both not shown) or any other such apparatus that promotes gas delivery. The gas may be further heated while passing through inspiratory limb 22 to breathing attachment 32 by limb heater element 34 associated with inspiratory limb 22. Expiratory limb 24 allows exhaled air and other gas expelled from patient 12 to pass back to ventilator 14, the atmosphere or elsewhere. A connecting member or joint 33 couples a first end of expiratory limb 24 to ventilator 14, and a second end of expiratory limb 24 is coupled to breathing attachment 32. Another limb heater element 36 is associated with expiratory limb 24 for heating the expelled gas. In the embodiment shown herein, limb heater element 34 and limb heater element 36 can be substantially identical, each could be comprised of one or more elongated heater wires having the same specific watt density(ies). Alternatively, the watt density of the heater wire(s) of limb heater element 34 could be different from the watt density of the heater wire(s) of limb heater element 36. Further alternatively, different types of heater elements or wire configurations could be employed for limb heater element 34 and/or 36.

Respiratory system 10 also includes a patient temperature cable (PTC) 38 having one or more temperature responsive devices such as thermistor-containing probes as at 40, 41 to provide thermal feedback in the form of temperature readings to heater unit 18 so a determination of necessary heating increase of decrease can be made. Temperature cable 38 includes a first communication cable 42 and a second communication cable 44. Temperature probe 41 is coupled to joint 30 at the entry to inspiratory limb 22 to provide a temperature reading via first communication cable 42 indicative of the actual measured temperature of the heated and humidified gas exiting from chamber 20 ("the output temperature"). Temperature probe 40 is coupled to breathing attachment 32 at the exit of inspiratory limb 22 to provide a temperature reading via second communication cable 44 indicative of the actual measured temperature of the humidified gas being provided to the patient ("the patient temperature"). First communication cable 42 has an end 48 electrically coupled to heater unit 18 to communicate "the output temperature" to controller 50. Similarly, second communication cable 44 has an end 52 electrically coupled to heater unit 18 to communicate "the patient temperature" to controller 50. Ends 48 and 52 may be advantageously secured together through a connector 54 to facilitate coupling the first and second cables 42, 44 to a mating socket (not shown) on heater unit 18. It should be noted that more than two such temperature cables could be used to facilitate the measurement of temperature at other locations. Further details of one suitable cable 38 are set out in concurrently filed U.S. patent application Ser. No. 11/927,020, and concurrently filed U.S. patent application Ser. No. 11/927,077, the disclosures of both of which are incorporated herein in their entirety by reference.

Heater unit 18 includes controller 50 and a heater 56. Thermally coupled to heater 56 is a temperature responsive device such as a thermistor to provide readings of the actual measured temperature of heater 56 to controller 50 ("the input temperature"). "The input temperature" is representative of the heat input to the chamber 20, and may be used as a heat input value. Controller 50 is in communication 58 with joint 33 on ventilator 14, as well as in communication 60 with joint 30 on humidification system 16. An example of one suitable heater 56 is described in concurrently filed U.S. patent application Ser. No. 11/926,982 the disclosure of which is incorporated herein by reference in its entirety. The output temperature readings and the patient temperature readings are also coupled to controller 50 via connector 54 and lines 63 and 65, and are utilized as appropriate for controlling heater 56 and limb heater elements 34 and 36 such as shown in concurrently filed U.S. patent application Ser. No. 11/926,990; U.S. patent application Ser. No. 11/927,000; U.S. patent application Ser. No. 11/927,013; U.S. patent application Ser. No. 11/927,054; and U.S. patent application Ser. No. 11/927,068 the disclosures of all five of which are incorporated herein by reference in their respective entirety.

Figure 2A:
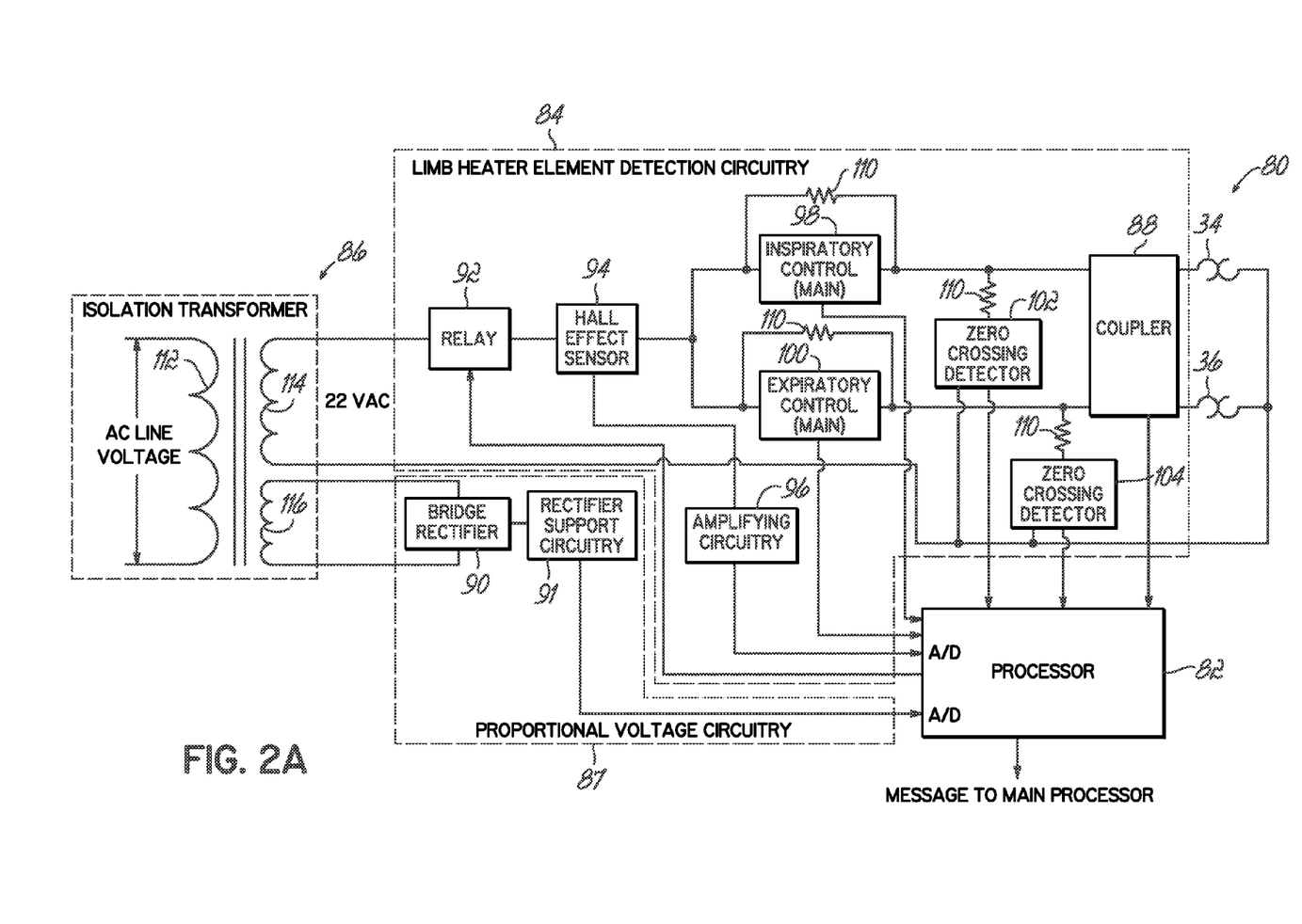
FIGS. 2A and 2B are schematic diagrams for purposes of explaining the heated breathing circuit detection feature of FIG. 1.

Controller 50 includes, as seen in greater detail in FIG. 2A, respiratory limb heater element detection system 80. Respiratory limb heater element detection system 80 includes a processor 82, which may be a microprocessor or other computer or programmable logic device that can be operatively associated with the limb heating elements 34 and/or 36. The limb heater element resistances are determined by the processor 82 via limb heater element detection circuitry 84. The limb heater elements 34 and/or 36 resistances determined by the processor 82 allow the processor to determine the type or nature of limb heater elements 34 and 36, for example adult, pediatric or neonate. Additionally, the processor 82 is able to determine the presence of limb heater elements 34 and/or 36 by checking whether zero crossings occur during heater operational modes by detecting the presence of an AC signal.

FIG. 2A is a schematic overview of the respiratory limb heater element detection system 80 contained within the controller 50. In one embodiment, respiratory limb heater element detection system 80 comprises a power source such as an isolation transformer 86, processor 82, proportional voltage circuitry 87 operatively associated with isolation transformer 86 and processor 82, limb heater element detection circuitry 84 operatively associated with isolation transformer 86 and processor 82, inspiratory limb heater element 34 operatively associated with limb heater element detection circuitry 84 via coupler 88, and expiratory limb heater element 36 operatively associated with limb heater element detection circuitry 84 via coupler 88. Respiratory limb heater element detection system 80 can sense whether inspiratory heater element 34 alone is in operative communication with humidification system 10 or whether both inspiratory limb heater element 34 and expiratory limb heater element 36 are in operative communication with humidification system 10. This is done using digital bits contained within coupler 88 as will be described in greater detail below. Controller 50 then determines whether to energize inspiratory limb heater element 34 alone or to also energize expiratory limb heater element 36.

Additionally, proportional voltage circuitry 87, operatively connected to isolation transformer 86, contains bridge rectifier 90, in operable communication with processor 82 via rectifier support circuitry 91. Bridge rectifier 90 is used to convert the alternating current from isolation transformer 86 to a direct current capable of being input into processor 82 as a proportional voltage. This proportional voltage allows processor 82 to determine if the power supplied by isolation transformer 86 to limb heater element detection circuitry 84 is within a proper range stored on processor 82. In other words, if the proportional voltage sent to processor 82 from proportional voltage circuitry 84 is not within a preset range, processor 82 will detect that there is an error in the system and will take a corrective action, e.g. shut down the system.

Limb heater element detection circuitry 84 is operatively connected to isolation transformer 86, processor 82, and inspiratory and expiratory limb heater elements 34, 36 via coupler 88. Limb heater element detection circuitry 84 includes, in one embodiment, relay 92, Hall Effect sensor 94, amplifying circuitry 96, inspiratory and expiratory controllers 98, 100, and inspiratory and expiratory zero crossing detectors 102, 104. Inspiratory and expiratory controllers 98, 100 are in operable communication with inspiratory and expiratory limb heater elements 34, 36 and zero crossing detectors 102, 104. The controllers 98, 100 selectively determine if only inspiratory limb heater element 34 is to receive power, or if both inspiratory and expiratory limb heater elements 34, 36 are to receive power from isolation transformer 86. The decision to only allow inspiratory controller 98 to transmit power to its respective limb heater element 34, or to allow both the inspiratory and the expiratory controllers 98, 100 to transmit power to their respective limb heater elements 34, 36, is decided by processor 82 by determining which of the two limb heater elements is present as will be described in greater detail below. In other words, the command to turn on a single limb heater element, inspiratory limb heater element, or both limb heater elements 34, 36, inspiratory and the expiratory limb heater elements 34, 36, is decided by processor 82 which then sends the command to inspiratory and expiratory controllers 98, 100 and controllers 98, 100 allow power to be transmitted from isolation transformer 86 to the appropriate limb heater elements 34, 36.

Limb heater element detection circuitry 84 also contains relay 92 that acts as a safety shut off. Relay 92 is in operative communication with the isolation transformer 86 and inspiratory and expiratory controllers 98, 100. Additionally, relay 92 has an input from processor 82. This allows processor 82, to send a command that allows relay 92 to complete the circuit it is in operative communication with, or to open the circuit it is in operative communication with. In other words, if processor 82 detects an error in respiratory limb heater element detection system 80, processor 82 can terminate operation. For example if inspiratory and expiratory controllers 98, 100 were to malfunction, processor 82 can send a command to relay 92 that will open the circuit and prevent inspiratory and expiratory controllers 98, 100 from receiving power and prevent the malfunctioning inspiratory and expiratory controllers 98, 100 from causing damage.

The Hall effect sensor 94 detects the current present in limb heater element detection circuitry 84 when either the inspiratory or expiratory controller 98, 100 is activated and outputs a voltage waveform that is proportional to the current detected. The output voltage waveform is then filtered and scaled by amplifying element 96 for analog to digital conversion by processor 82. Hall Effect sensor 94 an analog representation of the current in either inspiratory or expiratory limb heater elements 34, 36, in the form of a voltage signal, while being powered by the isolation transformer 86.

Additionally, limb heater element detection circuitry 84 also contains zero crossing detectors 102 and 104 in operable communication with controllers 98 and 100 and limb heater elements 34 and 36 via coupler 88. Zero crossing detectors 102, 104 are used to detect the presence of inspiratory and expiratory limb heater elements 34, 36 in respiratory limb heater element detection system 80. Additionally, bypass elements 110, e.g. a 3 K-ohm resistor, are present to drop any voltages present when inspiratory and expiratory limb heater elements 34, 36 are attached and inspiratory and expiratory controllers 98, 100 are in the process of detecting limb heater elements 34, 36.

Additionally, limb heater element detection circuitry 84 includes coupler 88 that is in operable communication with inspiratory limb heater element 34 if the device is operating in single limb operation. Coupler 88 can also be configured to work in a dual limb operation mode. In this configuration, inspiratory limb heater element 34 and expiratory limb heater element 36 are in operative communication with coupler 88. Coupler 88 allows heater elements with different resistances and heating capacities to be attached to the limb heater element detection circuitry 84 depending upon the needed application, e.g. adult, pediatric, or neonate heater elements.

Figure 2B:
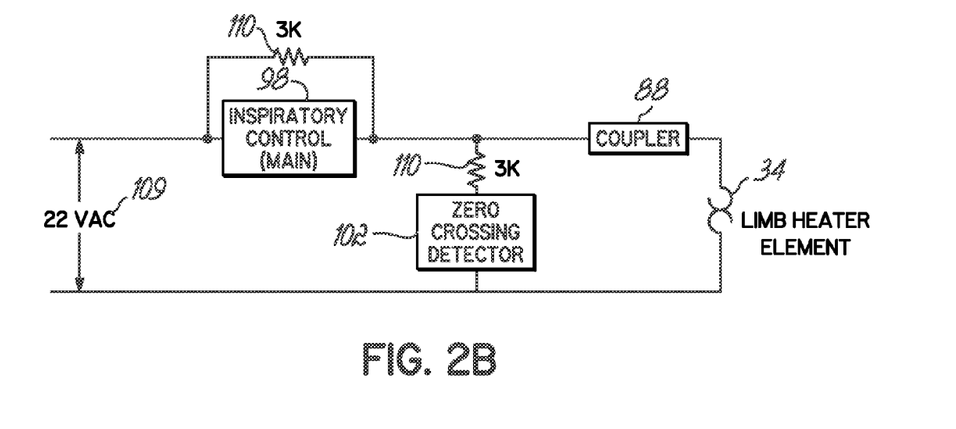

Referring now to FIG. 2B, a more detailed explanation of zero-crossing detector 102 is provided. It should be noted that FIG. 2B represents the inspiratory portion of limb heater element detection circuitry 84, the expiratory portion operates in the same way. A zero crossing voltage divider method is used to generally detect the presence of limb heater elements 34, 36 for both inspiratory and expiratory limbs while the unit is operating, i.e. delivering power to the heater elements 34, 36 to detect failure or removal of the limb heater elements 34, 36. The zero crossing voltage divider method is used for both the inspiratory and expiratory limb heater element paths. When controller 50 turns off the 22 VAC drive voltage 109 via relay 92, zero crossings will be detected if the impedance of the limb heater element 34 is not detected. Zero crossings will not occur if limb heater element 34 is attached to limb heater element detection circuitry 84. The 3K bypass resistor 110 provides this function since it will drop almost the entire 22 VAC input 109 if limb heater element 34, having an impedance of roughly 12.5 to 34 ohms, is attached. When limb heater element 34 is removed, the bypass resistor 110 provides ample AC voltage to generate zero crossings. When controller 50 turns the 22 VAC drive voltage 109 on, zero crossings will always be generated. This configuration provides the capability to detect an open limb heater element due to failure or removal of the limb heater element from the heated humidifier unit 18. Limb heater element presence can be detected without having to energize the limb heater element. The processor 82 monitors the signal from zero crossing detector 102. The controller 50 can request the zero crossing detection status via a SPI Bus Command as it controls power to each limb heater element 34, 36. The following table summarizes the various states and how the software interprets the results for either the inspiratory or expiratory limbs:

| Triac State | Heated Wire Present? | Zero Crossings Present? | Result |
| --- | --- | --- | --- |
| On | Present | Yes | Success |
| On | Present | No | Error |
| On | Not Present | Yes | Success |
| On | Not Present | No | Error |
| Off | Present | No | Success |
| Off | Present | Yes | Error |
| Off | Not Present | Yes | Success |
| Off | Not Present | No | Error |

Figure 2C:
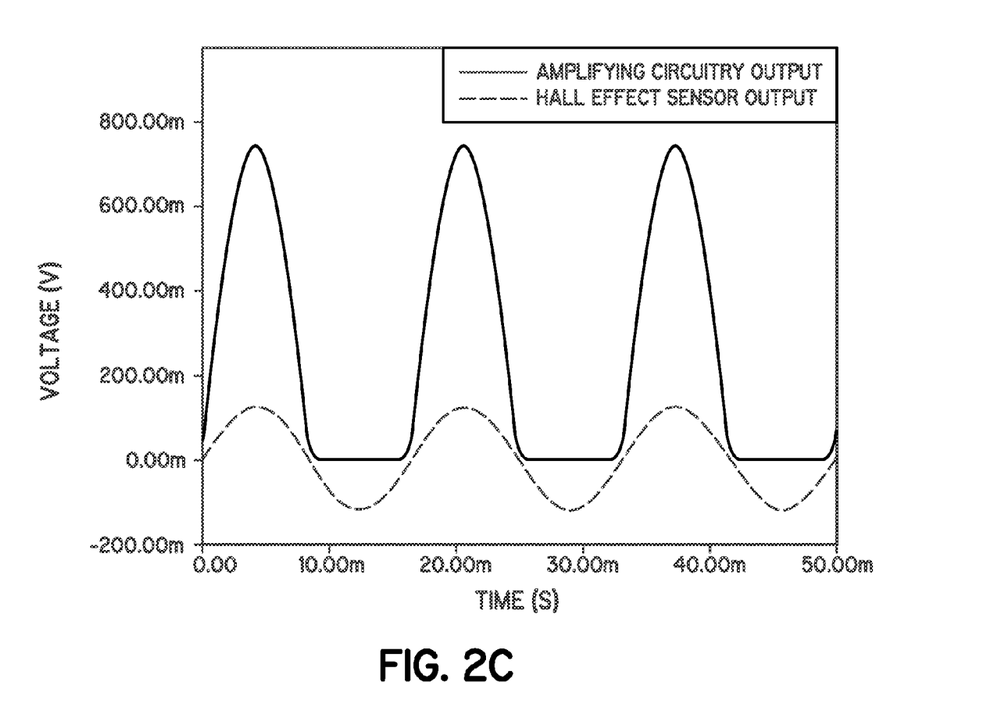
FIGS. 2C and 2D show exemplary waveforms of certain of the components shown in the schematic diagram of FIG. 2A for purposes of explaining operation of the heated breathing circuit detection feature of FIG. 1.

FIG. 2C is an example of the waveforms analyzed by the processor and used to determine the resistance of inspiratory and expiratory limb heater elements 34, 36. Hall effect sensor 94 is used to isolate the AC waveform applied to the limb heater elements 34, 36. The signal from Hall effect sensor 94 is amplified by amplifying circuitry 96 and applied to the processor 82 for analog to digital conversion. The output of the Hall Effect sensor 94 is shown as the dashed sine wave in FIG. 2C. The amplifying signal is shown as the solid amplifying circuitry signal in FIG. 2C.

The protection design provides the ability to determine wire resistance over a small number of AC cycles using actual current path current measurement. The fast capability of this approach allows the wire impedance to be determined in standby mode prior to operating without appreciably heating the air path.

Figure 2D:
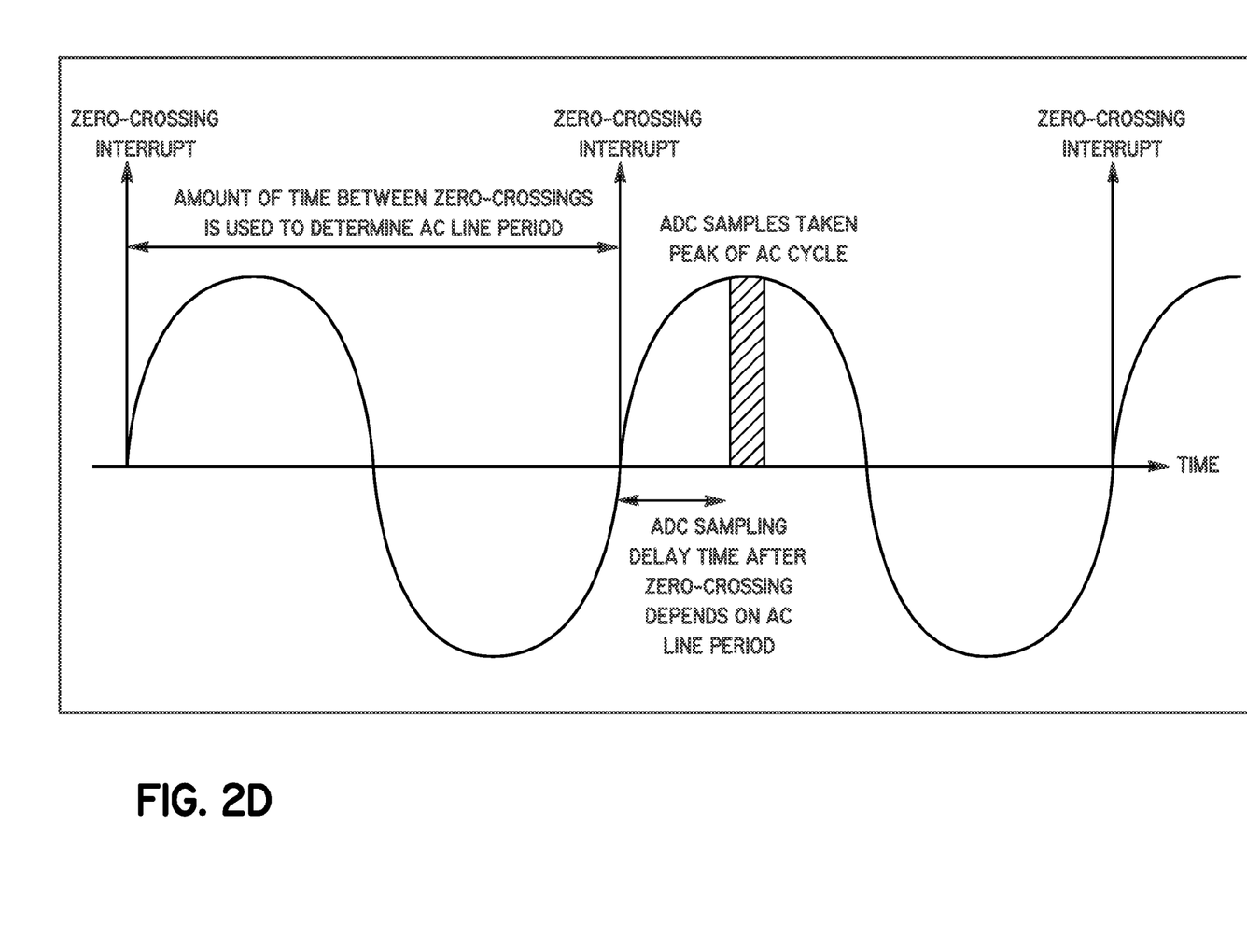

Referring now to FIG. 2d, a graph of several AC cycles is shown as well as the sample locations. Zero crossing detectors 102,104 detect both when the waveform has crossed from a negative to a positive voltage and the period length of a cycle. Processor 82 receives this information and, based on the period length, waits a quarter of a cycle to begin sampling the waveform. This insures that the samples are taken at the peak of the waveform. There can be as many as fifteen ADC samples taken at the peak of each AC cycle. The first thirteen ADC samples measure the Hall effect sensor 94 output voltage, which is directly proportional to the magnitude of the current flowing through limb heater elements 34, 36. The last two ADC samples measure the unregulated DC power supply voltage on the low-voltage secondary side 116 of the isolation power transformer 86, which is directly proportional to the magnitude of the voltage applied to the heated wire from the high-voltage secondary side 114 of the isolation power transformer.

The thirteen Hall effect sensor ADC samples are then averaged by the processor 82 to yield the (average) peak limb heater element current. In a similar fashion, the two DC power supply ADC samples are also averaged and multiplied by the voltage ratio between the isolation transformers high-voltage secondary 114 to low-voltage secondary side 116 to yield an (average) peak wire voltage.

By dividing the averaged peak heated wire voltage value by the averaged peak limb heater element current value, the instantaneous resistance of the limb heater elements 34, 36 can be determined. By turning on only one limb (expiratory or inspiratory) at a time, the resistance of each limb heater elements 34, 36 can be determined in an individual manner. This instantaneous limb heater element resistance is used to determine the type of limb attached (adult, neonate, etc.). The limb heater element resistance can also be checked against preset limits for each limb heater element type by the software and an error flag can be raised if the resistance is outside of the specific limits.

Figure 3A:
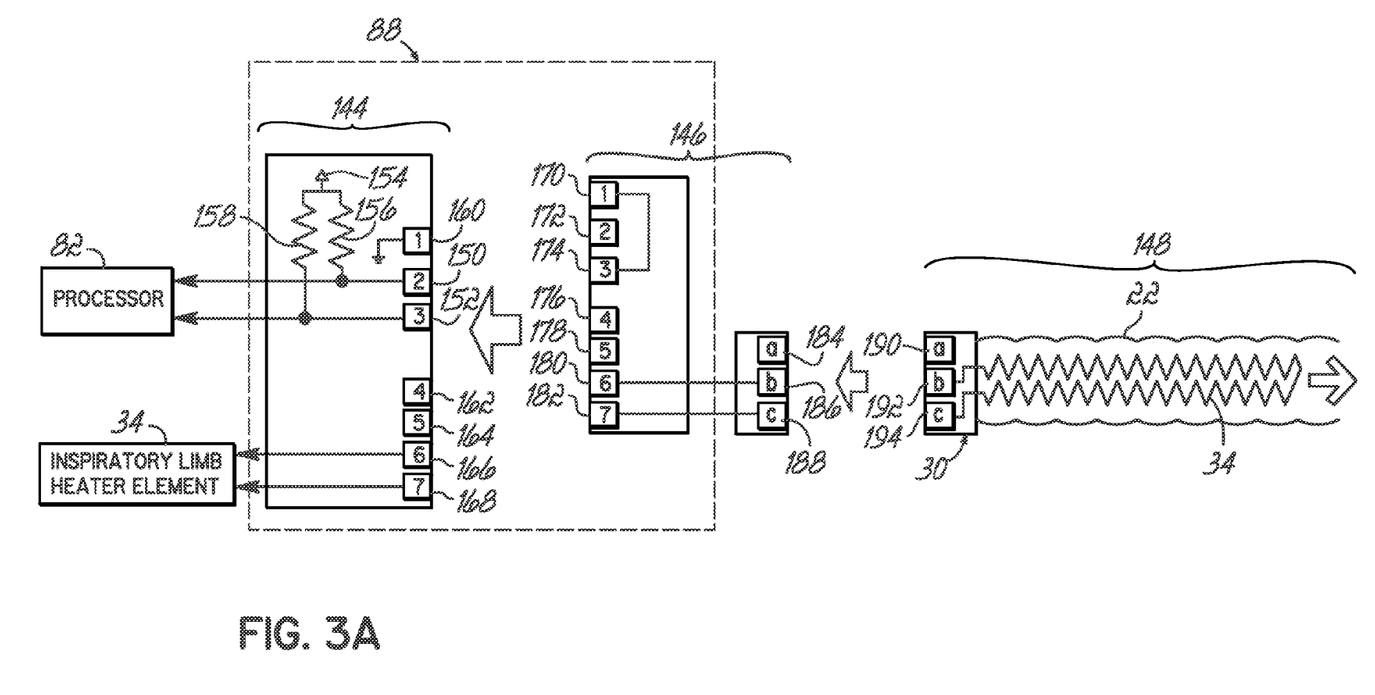
FIG. 3A is a schematic diagram showing a breathing circuit having only a heated inspiratory limb coupled to the heater unit of FIG. 1.
Figure 3B:
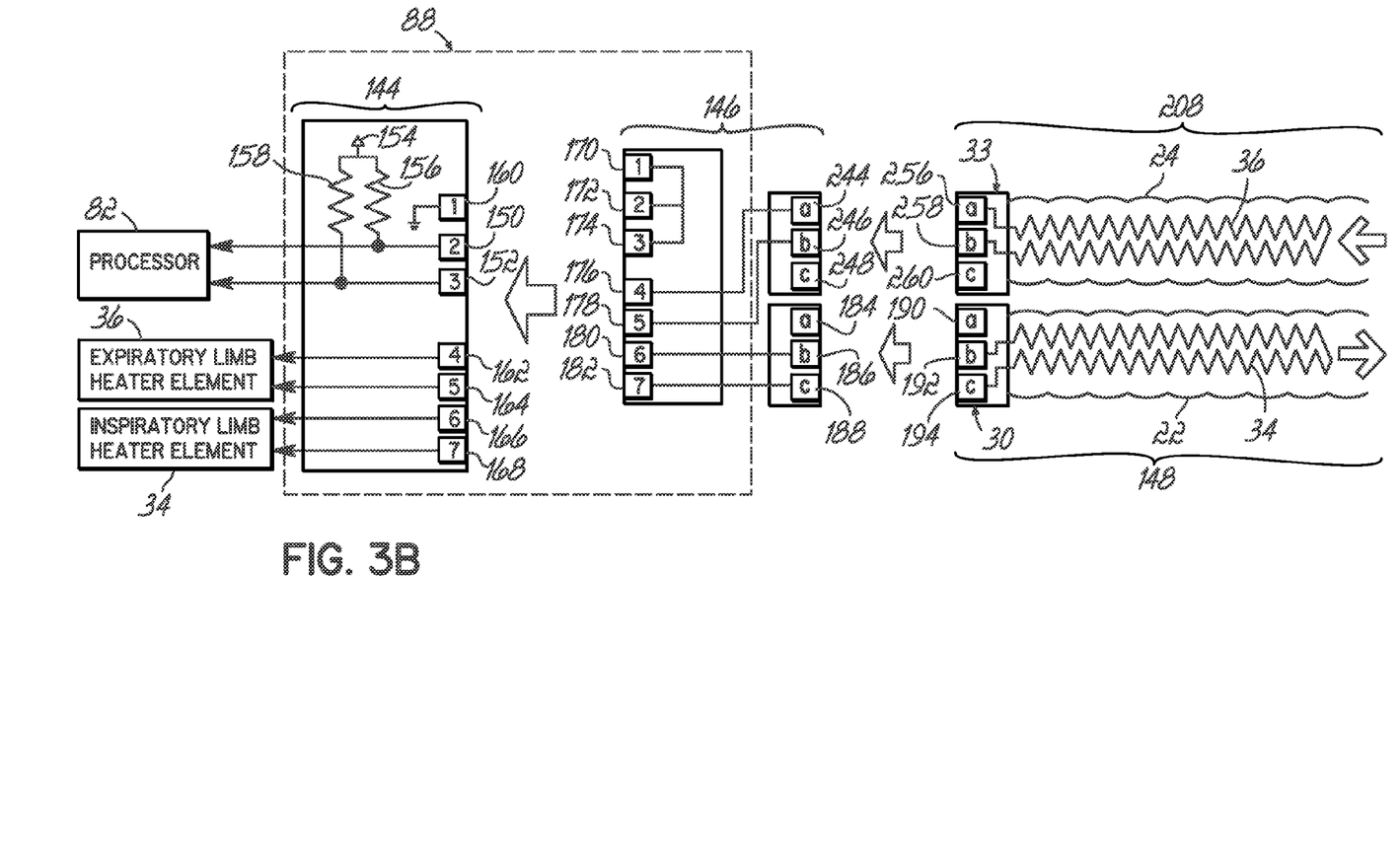
FIG. 3B is a schematic diagram showing a breathing circuit having a heated inspiratory limb and a heated expiratory limb coupled to the heater unit of FIG. 1.

Referring now to FIGS. 3A and 3B the respiratory limb heater element detection system 80 determines if it should be operating in non-heated wire mode, single limb mode, where only the inspiratory limb heater element 34 is required, or dual limb mode, where both the inspiratory and the expiratory heater elements 34, 36 are required. In one embodiment, as shown in FIG. 3A, limb heater element coupler 88 for single limb operation includes a limb heater element connector 144 and a single limb adapter cable 146 that is operatively connected to joint 30 of inspiratory limb assembly 148. The limb heater element connector 144 for single limb operation contains two pins 150, 152 that are each in operable communication with a voltage source 154 through separate resistors 156, 158. The two pins 150, 152 are capable of applying digital bits to processor 82 when they are in operable communication with the voltage source 154.

Limb heater element connector 144 for single limb operation also contains a pin 160 that is in operable communication with a ground source. Additionally, limb heater element connector 144 for single limb operation contains 4 pins 162, 164, 166, 168 that are in operable communication with the single limb adapter cable 146, and inspiratory and expiratory limb heater elements 34, 36.

The single limb adapter cable 146 comprises of seven pins 170, 172, 174, 176, 178, 180 and 182 to interface with limb heater element connector 144. The single limb adapter cable 146 also has three pins 184, 186, 188 that interface with inspiratory limb assembly 148 via joint 30. In order to indicate single limb operation to the processor 82 only one digital bit should be pulled low through pin 152. This is accomplished by ensuring that pin 172 is not connected to ground and only the pins 170 and 174 of single limb adapter cable 146 are in operable communication with the pins 160 and 152 of the heated wire connector 144. This allows the ground source of pin 160 to operatively communicate with pin 170 and complete a circuit through pins 174 and 152, which resultantly allows the processor 82 to see that one digital presence bit, namely 174, has been pulled low.

In order to indicate single limb operation to limb heater element detection circuitry 84 pins 176, 178, and 184 of single limb adapter cable 146 are left unconnected and pins 180 and 182 are of single limb adapter cable 146 are operatively connected to pins 186, 188 respectively of single limb adapter cable 146 and, thusly, connected to pins 166 and 168 of limb heater element connector 144.

Joint 30, of inspiratory limb assembly 148, comprises pins 190, 192, 194, and inspiratory limb heater element 34. The inspiratory limb assembly 148 is in operable communication with adapter cable 146 through pins 192,194 of joint 30 and pin 190 is left unconnected. During normal single limb operation inspiratory limb assembly 148 is in operable communication with single limb adapter cable 146 through pins 184, 186, and 188 of single limb adapter cable 146 and pins 190, 192, and 194 on joint 30 of inspiratory limb assembly 148.

When the three components, limb heater element connector 144, the single limb adapter cable 146, and inspiratory limb assembly 148, are all attached the power from limb heater element detection circuitry 84 travels through pins 166 and 168 of limb heater element connector 144, through pins 180, 182, 186, 188 of single limb adapter cable 146, and into pins 192, 194 on joint 30 of inspiratory limb assembly 148 which heats inspiratory limb heater element 34.

In another embodiment coupler 88 for dual limb operation, such as illustrated by FIG. 3B, coupler 88 comprises limb heater element connector 144 on, dual limb adapter cable 146, and is operatively connected to inspiratory limb assembly 148 via joint 30, and expiratory limb assembly 208 via joint 33. Limb heater element connector 144 for dual limb operation contains 2 pins 150, 152 that are each in operable communication with voltage source 154, through separate resistors 156 and 158, the processor 82, and the dual limb adapter cable 146. The two pins 150, 152 are capable of sending digital bits to the processor when they are in operable communication with voltage source 154.

Limb heater element connector 144 for dual limb operation also contains a pin 160 that is in operable communication with a ground source and the dual limb adapter cable 146. Additionally, limb heater element connector 144 for dual limb operation contains 4 pins 162, 164, 166, 168 that are in operable communication with dual limb adapter cable 146, and inspiratory and expiratory limb heater element 34, 36.

Dual limb adapter cable 146 comprises of seven pins 170, 172, 174, 176, 178, 180 and 182 to interface with limb heater element connector 144. Dual limb adapter cable 146 also has six pins 244, 246, 248, 184, 186 and 188 that interface with inspiratory and expiratory limb assemblies 148, 208. In order to indicate dual limb operation to processor 82 both pins 150, 152 should be pulled low to indicate two low digital bits. This is accomplished by ensuring that pins 170, 172, 174 of dual limb adapter cable 144 are in operative communications with the pins 150, 152, 160 of limb heater element connector 144. This allows the ground source of pin 160 to operatively communicate with pin 170 and complete a circuit through pins 172, 174, 150, 152, which allows processor 82 to see that two digital presence bits have been pulled low.

In order to indicate dual limb operation to limb heater element detection circuitry 84 the pins 248, 184 of dual limb adapter cable 146 are left unconnected and pins 176, 178 are operatively connected to pins 244, 246 of dual limb adapter cable 146 and pins 162, 164 of limb heater element connector 144. Additionally, pins 180, 182 are operatively connected to pins 186, 188 of dual limb adapter cable 146 and pins 166, 168 of limb heater element connector 144.

Inspiratory limb assembly 148 comprises the pins 190, 192, 194, and inspiratory limb heater element 34 on joint 30. Inspiratory limb assembly 148 is in operable communication with inspiratory limb heater element 34 through pins 192, 194 and is in operable communication with dual limb adapter cable 146 through pins 192, 194 on joint 30 and pin 190 is left unconnected.

Expiratory limb assembly 208 comprises of the pins 256, 258, 260, and expiratory limb heater element 36 on joint 33. Expiratory limb assembly 208 is in operable communication with dual limb adapter cable 146 through pins 256, 258 on joint 33 and pin 260 is left unconnected.

During normal dual limb operation inspiratory limb assembly 148 is in operable communication with dual limb adapter cable 146 through pins 184, 186, 188 of dual limb adapter cable 146 and pins 190, 192, and 194 on joint 30 of inspiratory limb assembly 148. Additionally, expiratory limb assembly 208 is in operable communication with dual limb adapter cable 146 through pins 244, 246, 248 of dual limb adapter cable 146 and pins 256, 258, 260 on joint 33 of expiratory limb assembly 208.

When the four components, heated wire connector 144, dual limb adapter cable 146, inspiratory limb assembly 148, and expiratory limb assembly 208, are all attached the power from limb heater element detection circuitry 84 travels through pins 162, 164, 166, 168 of limb heater element connector 144, through pins 176, 178, 180, 182, 244, 246, 186, 188 of dual limb adapter cable 146, and into pins 192, 194 of inspiratory limb assembly 148 which heats inspiratory limb heater element 34, and into pins 256, 258 of expiratory limb assembly 208 which heats expiratory limb heater element 36.

Figure 4:
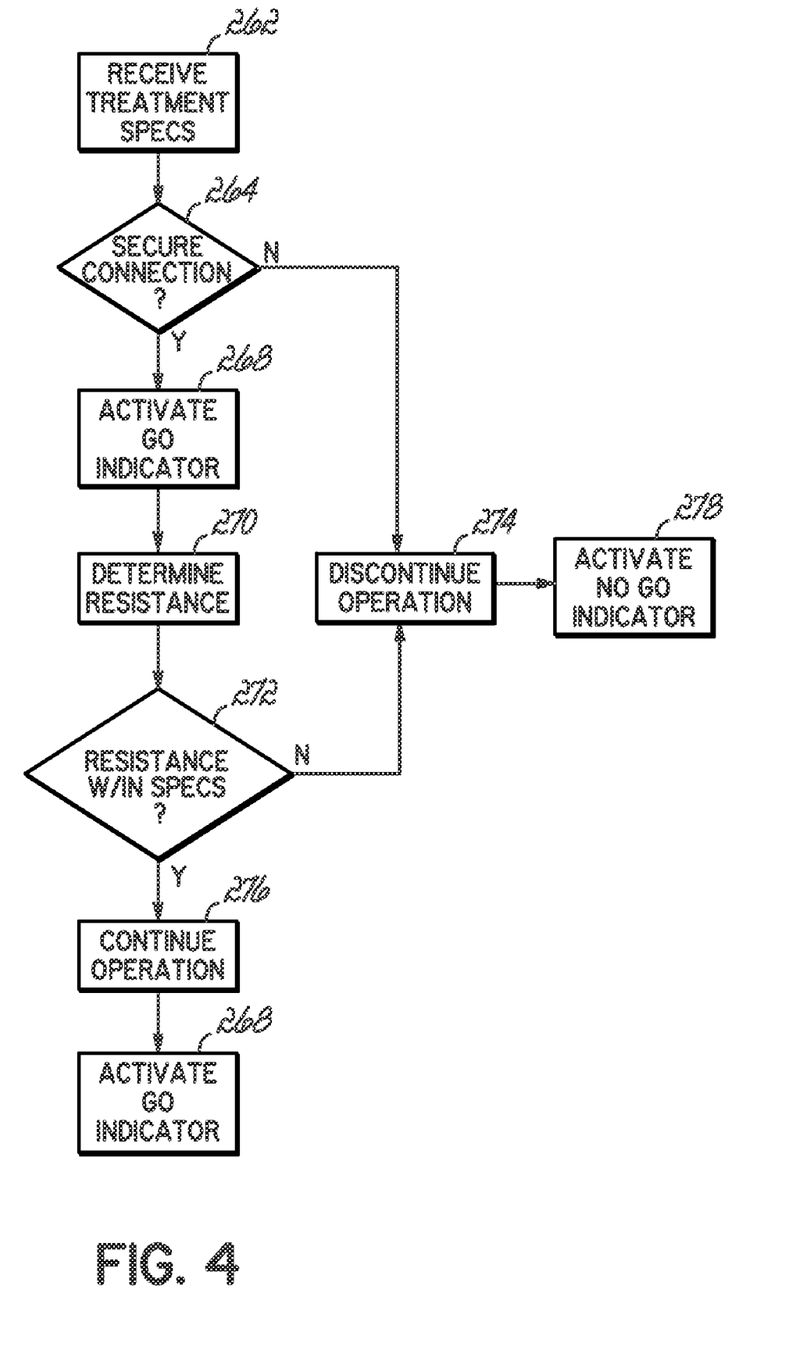
FIG. 4 is a flowchart describing operation of the heated breathing circuit detection feature of FIG. 1 in accordance with the principles of the present invention.

FIG. 4 is a flowchart having a sequence of steps executable by the system of FIG. 1 for conducting a detection application. In summary, the system senses an adaptor cable identification prong or prongs coupled to the heated hose wire, and registers. The system registers from the prong(s) whether the limb heater element configuration is single or dual limb, and activates an alarm if a connection is not made. As a separate part of the verification process, the system determines the type of limb heater element that is connected, based on at least one of the adapter cable identification bits of the adaptor cable identification and a sensed resistance or current. The system will activate a go indicator if the connection is proper. Alternatively, the system will illuminate a no-go indicator or otherwise activate an alarm if current is improper. The alarm may prompt or automatically halt the process.

At step 262, the heater unit 18 determines the type of patient receiving treatment, e.g. adult or neonate and sets the operational mode of the unit 18 in response to an electronic key (not shown) associated with the patient temperature cable (PTC) 38. The system may correlate the electronic key information to stored specifications particular to that type of patient. For instance, such specifications may include a stored resistance or range of acceptable resistances that will be recalled and compared to the determined resistance to verify that the correct limb has been connected for the particular type of patient identified by the electronic key.

The system verifies at step 264 that the limb is securely attached. If the bits of the connection are not securely attached, then the go indicator will not activate, operation can discontinue 274 and an alarm may sound and/or a no-go indicator will initiate 278. Otherwise, a go indication is initiated 268 and operation will continue. As discussed herein, the system becomes aware of the configuration, e.g. dual or single limb, from the connection at step 264.

The resistance of the connected limb(s) can be determined at step 270. The system may compare at step 272 whether this determined resistance matches to an expected resistance or is within a range of acceptable resistances for the type of patient. If the comparison is favorable, then operation may continue at step 276 and a go indication initiated at step 268. The system repeats the sequence until the resistance is different from the stored resistance or is outside the range of acceptable resistances at which time operation will discontinue at step 274 and a no-go indicator will be initiated at step 278.

While the invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. By way of example, the temperature readings made using a thermistor could likewise be made using a thermocouple or any other such temperature measurement means. Additionally, while ventilator 14 is shown as driving the gas through chamber 20, it will be appreciated that other gas systems could be employed, such as from a hospital oxygen supply, a CPAP or BiPAP pump, or other air or oxygen pumping system. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. A humidification system comprising:
   a heater unit configured to heat liquid contained within a chamber supported by the heater unit;
   a breathing circuit fluidly connected to the chamber;
   a heating element electrically coupled to the heater unit and supported by the breathing circuit, the heating element being configured to add heat to a gas passing through the breathing circuit; and
   a detection system electrically coupled to the heating element, the detection system having a processor configured to determine a resistance of the heating element and detect in relation thereto the breathing circuit type.

2. The humidification system of claim 1, further comprising a power source configured to supply power to the heating element, the power source having a primary, a first secondary electrically coupled to the heating element, and a second secondary electrically coupled to the processor.

3. The humidification system of claim 2, wherein the detection system further comprises a sensor electrically coupled to the first secondary and the processor, the sensor being configured to apply a signal to the processor that is indicative of a current passing through the heating element.

4. The humidification system of claim 3, wherein the sensor comprises a Hall Effect sensor and the signal applied to the processor comprises a voltage signal.

5. The humidification system of claim 3, wherein the second secondary applies a voltage signal to the processor, and further wherein the processor is configured to determine a voltage of the heating element from the voltage signal applied by the second secondary.

6. The humidification system of claim 5, wherein the processor is configured to determine the resistance of the heating element from the signal applied by the sensor and the voltage signal applied by the second secondary.

7. The humidification system of claim 1, wherein the processor is configured to detect the type of breathing circuit by comparing the determined resistance of the heating element to at least one predetermined resistance or range of resistances.

8. The humidification system of claim 2, further comprising a relay electrically coupled to the first secondary and the heating element, the relay being configured to enable and disable power to the heating element in response to the detection system.

9. The humidification system of claim 2, further comprising at least one zero-crossing detector electrically coupled to the first secondary and the processor.

10. The humidification system of claim 9, wherein the detection system is configured to determine a disconnection of the heating element from the heater unit in response to a signal applied from the zero-crossing detector to the processor.

11. The humidification system of claim 9, wherein the detection system is configured to determine a failure of the heating element in response to a signal applied from the zero-crossing detector to the processor.

12. A respiratory system comprising:
   a breathing circuit including at least one of an inspiratory limb and an expiratory limb;
   a heating element supported by the at least one inspiratory limb and expiratory limb, the heating element being configured to add heat to a gas passing through the at least one inspiratory limb and expiratory limb;
   a connection device configured to couple with the at least one inspiratory limb and expiratory limb; and
   indicia associated with the connection device for identifying the presence of the at least one inspiratory limb and expiratory limb, the indicia having an electrical characteristic.

13. The respiratory system of claim 12, further comprising:
   a ventilator;
   a humidification system fluidly connected to the ventilator, the humidification system including a heater unit configured to heat liquid contained within a chamber supported by the heater unit; and
   an inspiratory limb fluidly connected to the chamber.

14. The respiratory system of claim 13, further comprising:
   an expiratory limb fluidly connected to the ventilator.

15. The respiratory system of claim 12, the connection device including three pins at least two of which being electrically coupled together within the connection device to define the electrical characteristic.

16. The respiratory system of claim 15, all of the three pins being electrically coupled together within the connection device to define the electrical characteristic.

17. The respiratory system of claim 15, a third of the three pins being uncoupled electrically to the at least two pins within the connection device.

18. The respiratory system of claim 12 further comprising a detection system electrically coupled to the connection device, the detection system having a process configured to detect the breathing circuit type in relation to the electrical characteristic of the indicia.

19. A method for detecting a type of breathing circuit in a humidification system, the breathing circuit having a heating element supported thereby, comprising:
   determining a resistance of the heating element;
   associating at least one predetermined resistance or range of resistances with at least one breathing circuit type; and
   comparing the determined resistance of the heating element to the at least one predetermined resistance or range of resistances so as to detect the breathing circuit type.

20. The method of claim 19, wherein the breathing circuit type comprises one of adult, pediatric and neonate.

21. The method of claim 19, wherein the determining step comprises:
   determining a current passing through the heating element;
   determining a voltage of the heating element; and
   calculating the resistance of the heating element from the determined current and voltage.

22. The method of claim 21, wherein the current is determined from a voltage signal applied by a Hall Effect sensor.

23. The method of claim 15, wherein the resistance of the heating element is determined prior to substantial heating of the heating element.

24. A method of identifying a breathing circuit having a heating element supported thereby, comprising: connecting the breathing circuit to a humidification system through a connection device, the connection device having indicia associated therewith, the indicia having an electrical characteristic;
   determining the electrical characteristic of the indicia with the humidification system; and detecting the breathing circuit type in relation to the determined electrical characteristic of the indicia.

25. The method of claim 24, wherein the breathing circuit comprises an inspiratory limb.

26. The method of claim 24, wherein the breathing circuit comprises an inspiratory limb and an expiratory limb.

27. A method of identifying a breathing circuit connected to a humidification system through a connection device, the breathing circuit having a heating element supported thereby, comprising associating indicia with the connection device, the indicia having an electrical characteristic, wherein associating indicia with the connection device comprises:
providing three pins in the connection device; and
electrically coupling together at least two of the three pins within the connection device to define the electrical characteristic.

28. The method of claim 27 further comprising electrically coupling together all of the three pins within the connection device to define the electrical characteristic.

29. The method of claim 27 further comprising leaving a third of the three pins uncoupled electrically to the at least two pins within the connection device.

30. The method of claim 24 further comprising detecting the breathing circuit type in relation to the electrical characteristic of the indicia.

* * * * *